(12) United States Patent
Nagel et al.

(10) Patent No.: US 6,413,733 B1
(45) Date of Patent: Jul. 2, 2002

(54) STABILIZED REAGENT AND METHOD FOR DETERMINING CREATINE KINASE

(75) Inventors: Rolf Nagel, Buerstadt; Juergen Mistele, Bruehl; Norbert Schroeder, Schwetzingen, all of (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/581,357

(22) PCT Filed: Dec. 9, 1998

(86) PCT No.: PCT/EP98/08016

§ 371 (c)(1),
(2), (4) Date: Jun. 9, 2000

(87) PCT Pub. No.: WO99/29895

PCT Pub. Date: Jun. 17, 1999

(30) Foreign Application Priority Data

Dec. 11, 1997 (DE) .......................................... 197 55 079

(51) Int. Cl.$^7$ .......................... C12Q 1/50; C12Q 1/48; C12Q 1/54; C12Q 1/00
(52) U.S. Cl. ............................. 435/17; 435/15; 435/14; 435/4
(58) Field of Search .............................. 435/17, 15, 14, 435/4

(56) References Cited

U.S. PATENT DOCUMENTS

| 4,888,289 | A | | 12/1989 | Takami et al. ................ 435/15 |
| 5,716,797 | A | * | 2/1998 | Danno et al. |

FOREIGN PATENT DOCUMENTS

| EP | 0 253 520 A2 | 1/1988 | ............ C12Q/1/54 |
| EP | 0 426 100 A1 | 5/1991 | ............ C12N/9/96 |
| EP | 0 596 218 B1 | 5/1994 | ......... G01N/33/573 |
| EP | 0 640 686 A2 | 3/1995 | ............ C12N/9/04 |
| EP | 0 686 561 A1 | 12/1995 | ........... B65B/61/20 |
| EP | 0 721 986 A2 | 7/1996 | ............ C12Q/1/50 |
| EP | 0 774 514 A1 | 5/1997 | ............ C12Q/1/50 |
| WO | WO 95/30769 | 11/1995 | ............ C12Q/1/50 |

OTHER PUBLICATIONS

Derwent Acc. No. 1997–520749, 1997. Solution–stable reagent for measuring activity of creatine kinase—contains creatine phosphoric acid, ADP, a thiol compound and a magnesium salt and sulfur dioxide derivative as a stabiliser.*
Abstract of Japanese Publication No. 61–289900, published Dec. 19, 1986 (1pp).
Abstract and computer–automated English translation of Japanese Publication No. 90–070298, published Mar. 18, 1997 (54pp).
Abstract of Japanese Publication No. JP10327895, published Dec. 15, 1998 (1pp).
Vormbrock, R., et al., "A New Method for the Determinatin of CK–MB Activity," Enzyme, vol. 38, Supplement 1, pp. 20–21 with cover sheet (3pp).

* cited by examiner

*Primary Examiner*—Ralph Gitomer
*Assistant Examiner*—Mahreen Chaudhry
(74) *Attorney, Agent, or Firm*—Marilyn L. Amick; Roche Diagnostics Corporation

(57) ABSTRACT

A stabilized reagent for the photometric enzymatic determination of creatine kinase (CK) in biological sample material by forming ATP from creatine phosphate and ADP and detecting the ATP formed, containing an organic or inorganic sulphur compound preferably in a submolar amount relative to the added CK activator. A corresponding reagent in a liquid form is stable at 2 to 8° C. for up to 12 months without significant loss of function.

14 Claims, 5 Drawing Sheets

STABILIZED REAGENT AND METHOD FOR DETERMINING CREATINE KINASE

Figure 1:
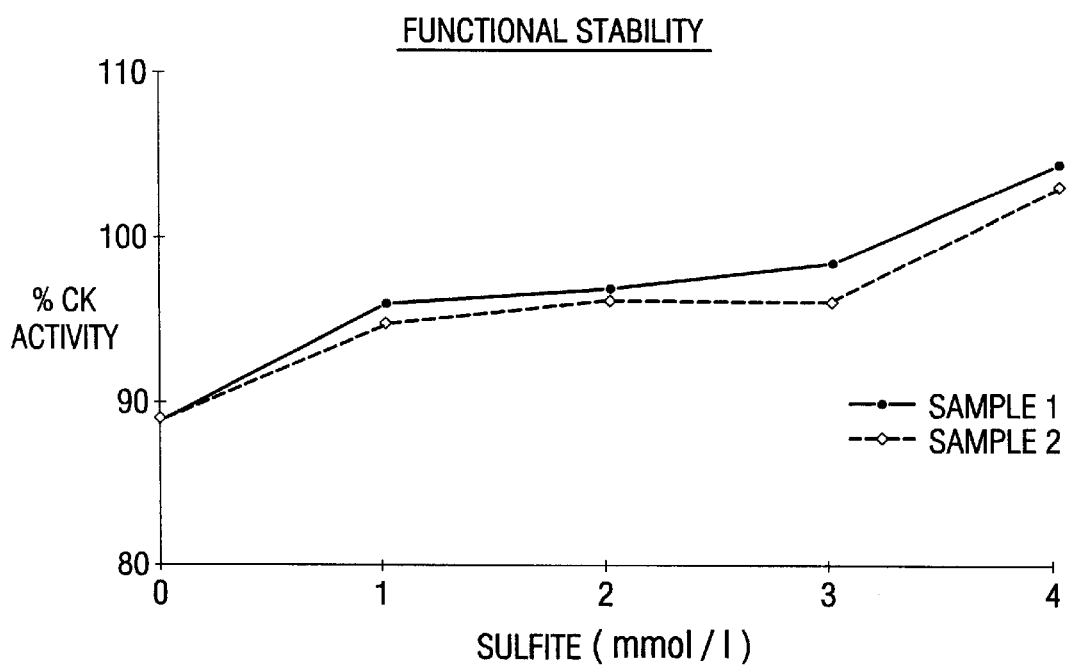

The invention concerns an improved method and stabilized reagent for the photometric determination of creatine kinase in biological samples such as in particular human blood serum or plasma. The reagent is essentially characterized in that it contains a substoichiometric amount of an organic or inorganic reducing sulphur compound.

The determination of creatine kinase in serum or plasma plays an important role in the diagnosis of cardiac infarction. A photometric test is used as a standard method for this in which adenosine 5'-triphosphate (ATP) and creatine are generated in coupled enzymatic reactions from creatine phosphate and adenosine 5'-diphosphate (ADP) by the creatine kinase (CK) contained in the sample; the ATP is for example used to form glucose-6-phosphate from glucose in the presence of hexokinase (HK) which is oxidized to gluconate-6-phosphate in a reaction catalysed by glucose-6-phosphate dehydrogenase (G6P-DH) while simultaneously converting $NAD^+$ or $NADP^+$ into NADH or NADPH:

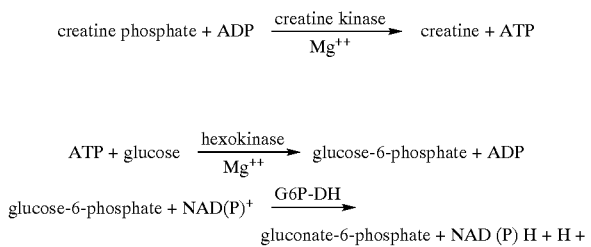

The measured quantity is the increase in absorbance caused by the formation of NAD(P)H in a specified time interval at a certain temperature, usually between 25 and 37° C., which is proportional to the CK activity in the sample volume. In order for the CK to develop its full enzymatic activity, the determination is usually carried out in the presence of CK activators for example thiol compounds such as glutathione, dithiothreitol, thioglycerol, 2-mercaptoethanol and N-acetyl cysteine.

Furthermore inhibitors for myokinases (adenylate kinase) that may be present in the sample such as adenosine-5'-monophosphate (AMP) and/or di-adenosine-pentaphosphate are preferably also added to the reagent for the CK test. Despite these additives unspecific ATP can be formed from ADP according to the following reaction:

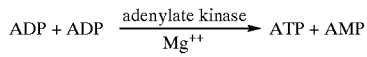

This can lead to an additional formation of NAD(P)H which falsifies the CK determination. Interference by incompletely inhibited adenylate kinase which can occur especially in haemolytic samples can be eliminated by determining the activity of adenylate kinase before actually starting the CK reaction by adding creatine phosphate and subtracting this (so-called rate blanking) from the total activity (CK and adenylate kinase). In this connection it is important that all components required to detect the ATP quantity formed by adenylate kinase are present in the first reaction solution (except for creatine phosphate).

Furthermore specific inhibitors such as antibodies directed against particular CK isoenzymes can also be added to the reagent for the determination of creatine kinase isoenzymes.

In order to increase the detection sensitivity the reagent forming glucose-6-phosphate and converting glucose-6-phosphate by means of $NAD(P)^+$ and G6P-DH can optionally additionally contain 6-phosphoglucono-lactonase and gluconate-6-phosphate dehydrogenase; in this case two moles of NADH or NADPH are generated per mole of ATP or glucose-6-phosphate formed (R. Vormbrock and R. Helger, Enzyme 38, Suppl. 1 (1987), p. 20/21).

In addition it is for example possible to carry out the CK test by converting the ATP formed from creatine phosphate and ADP into glycerol-3-phosphate using glycerol and glycerol kinase, preferably in the presence of magnesium ions, which is converted enzymatically in the presence of oxygen into hydrogen peroxide and is detected in the usual manner by means of peroxidase and redox indicators.

In principle all components required for the CK determination, i.e. enzymes and substrates, can be present in a single reagent. However, especially on analyzers the determination is preferably carried out by firstly preincubating the sample for several minutes with a first partial reagent which, apart from creatine phosphate, contains all components necessary for the detection reaction and other potential auxiliary substances such as N-acetyl cysteine, adenylate kinase inhibitors and optionally CK isoenzyme inhibitors and subsequently the detection reaction is started by adding a second partial reagent which essentially contains creatine phosphate in a buffered solution.

In addition to avoiding formation of NAD(P)H by CK during the phase in which the enzyme is activated in the presence of the added thiol compound, this also prevents possible falsification of the measured result by excessive activities of adenylate kinase that cannot be adequately inhibited by adenylate kinase inhibitors which can for example occur in haemolytic samples. For this purpose a first measurement of the rate of formation of NAD(P)H is carried out after mixing the sample and the first partial reagent and the result is subtracted from the rate of formation of NAD(P)H after adding the second partial reagent containing creatine phosphate.

A disadvantage for the user of such reagents is in particular that the reagents have to be firstly prepared before use by dissolving the solid components e.g. lyophilisates, granulates or tablets and moreover they are only stable for a few days or weeks even when stored cold between 2 to 8° C. As a result of rationalization in the clinical laboratory there is nowadays an increasing need for ready-to-use reagents with a shelf-life of at least 12 months at 2 to 8° C. At present this demand cannot be met due to lack of stability. The instability of the ready-to-use reagent is mainly caused by the instability of N-acetyl cysteine (NAC, activator of CK).

Although the stability problem can be resolved as described in EP 0 686 561 by storing NAC (together with NAD(P)) in a second solution at pH 3.0, this has considerable disadvantages. In this reagent formulation the CK is only activated when the CK reaction is started. Hence a longer waiting period is required before the actual start of the measurement in order to avoid the lag phase and this considerably limits the measuring range of the method. A further disadvantage is that it is not possible to eliminate the adenylate kinase interference by rate blanking. Measures for stabilizing liquid reagents suitable for the determination of CK are described in EP 0 774 514 such as the addition of a phosphine and a sulfhydryl compound such as dithiothreitol, DTT. However, a disadvantage of adding DTT is that it destabilizes the auxiliary enzyme G6P-DH and thus necessitates the addition of an additional component in the form of a hydroxylamine compound (for example carboxymethoxylamine hydrochloride) to stabilize the G6P-DH (EP 0 640 686).

Furthermore EP 0 721 986 describes stable reagents for the determination of creatine kinase which contains certain SH compounds such as thiolglycerol (TG), 2-mercaptoethanol (2ME) or 2-mercaptoethanesulfonic acid (2MES) in molar concentrations. In contrast to other activators these do not inhibit the CK activity in their oxidized form. However, relatively high concentrations of such SH compounds can have undesired side-effects such as the inactivation of auxiliary enzymes (e.g. G6P-DH). Consequently these activators are also at present not recommended by experts for the determination of the CK activity (e.g. according to the IfcC, DGkCh). Furthermore the comparability of such test systems is open especially with regard to the isoenzymes and CK from different species.

Consequently and especially to further rationalise work in the clinical laboratory under increasing cost pressure, there is today an increasing requirement for stabilized reagents which can be stored and are stable in a ready-to-use liquid form for at least 12 months at 2 to 8° C. without a renewed calibration and which largely eliminate the risk of unspecific reactions caused by certain additives.

This object is achieved by a reagent which contains a suitable buffer system, substrates and corresponding coenzymes that can be converted by CK, a CK activator and components required for one or several subsequent enzymatic reactions and an organic or inorganic sulphur compound or mixtures of corresponding sulphur compounds in a submolar amount relative to the CK activator. Appropriate CK activators are known to a person skilled in the art. A reagent is preferred according to the invention which contains creatine phosphate and adenosine 5'-diphosphate (ADP) as the substrates that can be converted by CK. A reagent is particularly preferred which contains glucose, an enzyme that forms glucose-6-phosphate such as hexokinase, ADP, creatine phosphate, a CK activator, optionally adenosine 5'-mono-phosphate, a coenzyme in an oxidized form such as $NAD^+$, $NADP^+$ or derivatives thereof, a G6P dehydrogenase and optionally one or several adenylate kinase inhibitors and/or other activators and a substoichiometric amount of one or several of the said sulphur components which are preferably reducing substances with a negative charge. In particular sulphur-oxygen compounds such as thiosulfate, dithionite, pyrosulphuric acid, polythionic acid and salts thereof are added according to the invention. Inventive salts that come into consideration are in particular oxygen acids of sulphur such as thiosulfates or sulfites of alkali and/or alkaline earth ions or sulfite-releasing compounds. Corresponding disodium salts have proven to be particularly advantageous for stabilizing reagents for the determination of CK.

The concentration of the inventive sulphur component in the reagent is usually of the same order of magnitude as that of the enzyme (CK) to be determined and is no more than 20 mmol/l. Concentrations of the sulphur component between ca. 0.01 and 5 mmol/l are preferred and 0.1 to 1.0 mmol/l is especially preferred.

All other components and optionally other auxiliary substances including the optionally added 6-phosphogluconolactonase and gluconate-6-phosphate dehydrogenase are used in the usual concentrations for a person skilled in the art.

A particular embodiment of the reagent according to the invention is when the components required for the CK determination are divided between two separate partial reagents whereby the first partial reagent contains all substances and enzymes required for the CK determination apart from creatine phosphate and the second partial reagent contains creatine phosphate and for example glucose. The sulphur component according to the invention and the CK activator can be present in the first and/or second reagent. It has proven to be advantageous to not add the sulphur component, e.g. via the second reagent solution, to the more complex first reagent which also contains the CK activator until immediately before the measurement.

A further special embodiment of the invention is a reagent which contains glucose in combination with NAD(P)+ and G6P-DH in a partial reagent at a low concentration preferably of ca. 5 mmol/l or less; ca. 0.5 to 1.0 mmol/l glucose is preferred.

The aqueous reagent according to the invention is characterized by exceptional stability after long storage between 2 and 8° C. i.e. over periods ranging from several months to 12 months without renewed calibration and by a high specificity. Thus in a test of CK function only a slight deviation was found compared to a freshly prepared reagent, i.e. the CK recovery rates were approximately 100%.

A further subject matter of the invention is a method for the enzymatic determination of creatine kinase in a biological sample material in the presence of one of the organic or inorganic sulphur compounds that are specified above in more detail.

Figure Legends:

FIG. 1: Determination of the CK activity with addition of $Na_2SO_3$ (0 to 4 mmol/l); storage period: 14 days, temperature: 35° C. compared to 2 to 8° C.

Figure 2:
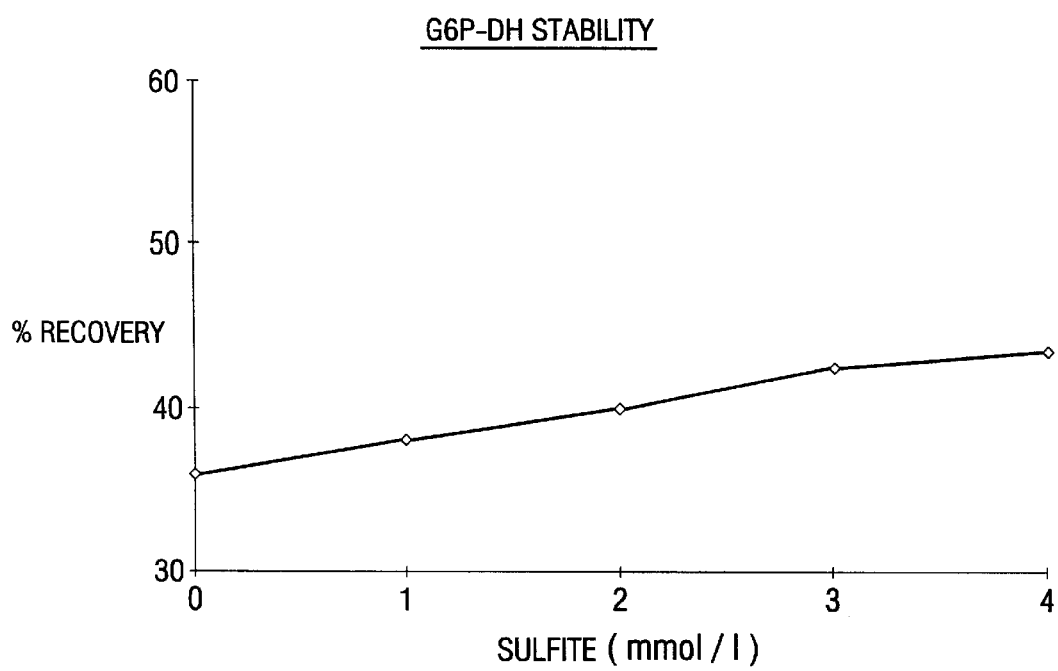

FIG. 2: Influence of $Na_2SO_3$ (0 to 4 mmol/l) on G6P-DH; storage period: 14 days, temperature: 35° C. compared to 2 to 8° C.

Figure 3:
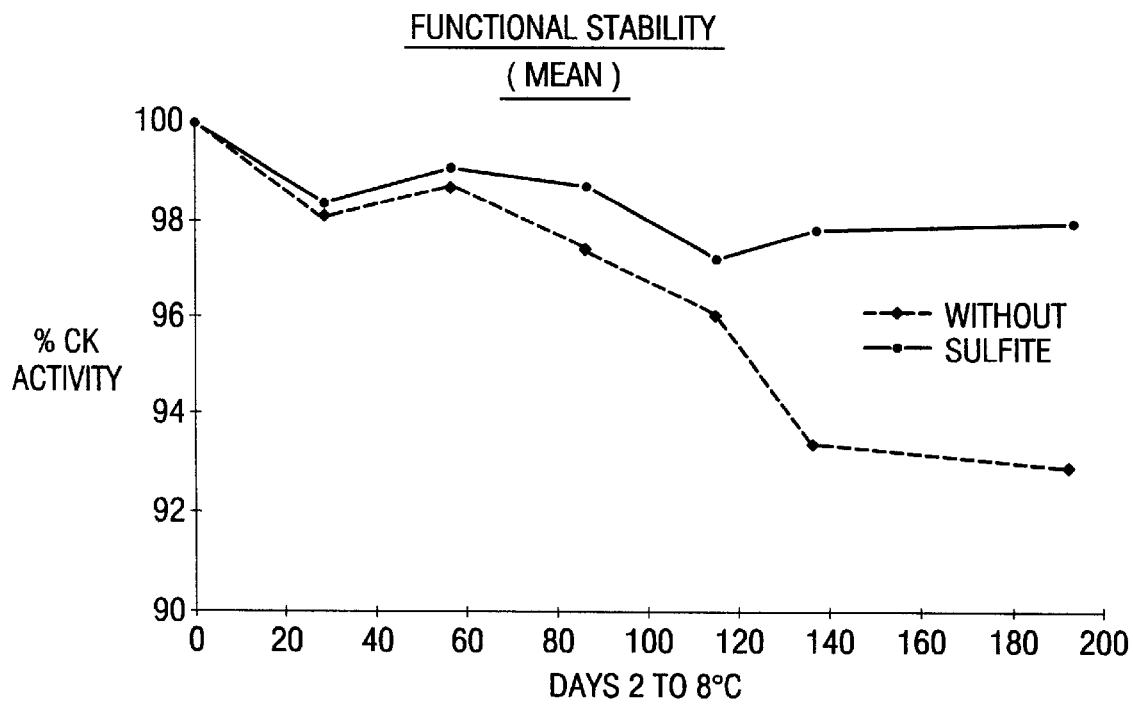

FIG. 3: Determination of the CK activity with addition of $Na_2SO_3$ (1 mmol/l) storage period: 192 days, temperature: 2 to 8° C. (2 samples).

Figure 4:
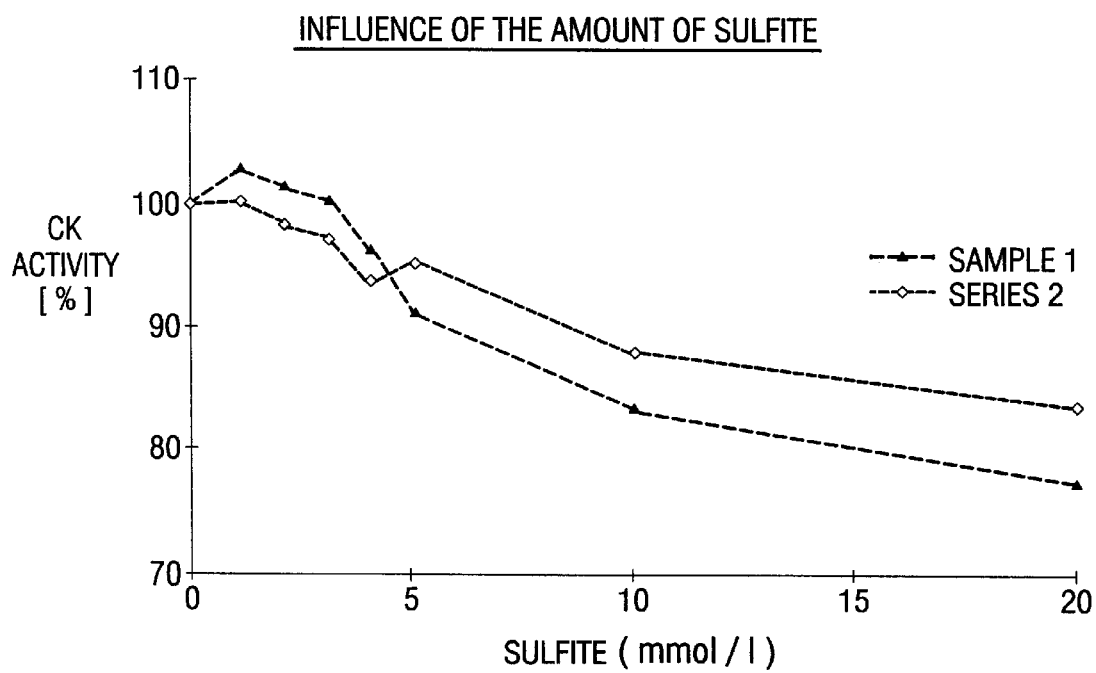

FIG. 4: Influence of various concentrations of $Na_2SO_3$ (0, 1, 2, 3, 4, 5, 10 and 20 mmol/l) on the CK activity; temperature: 2 to 8° C.

Figure 5:
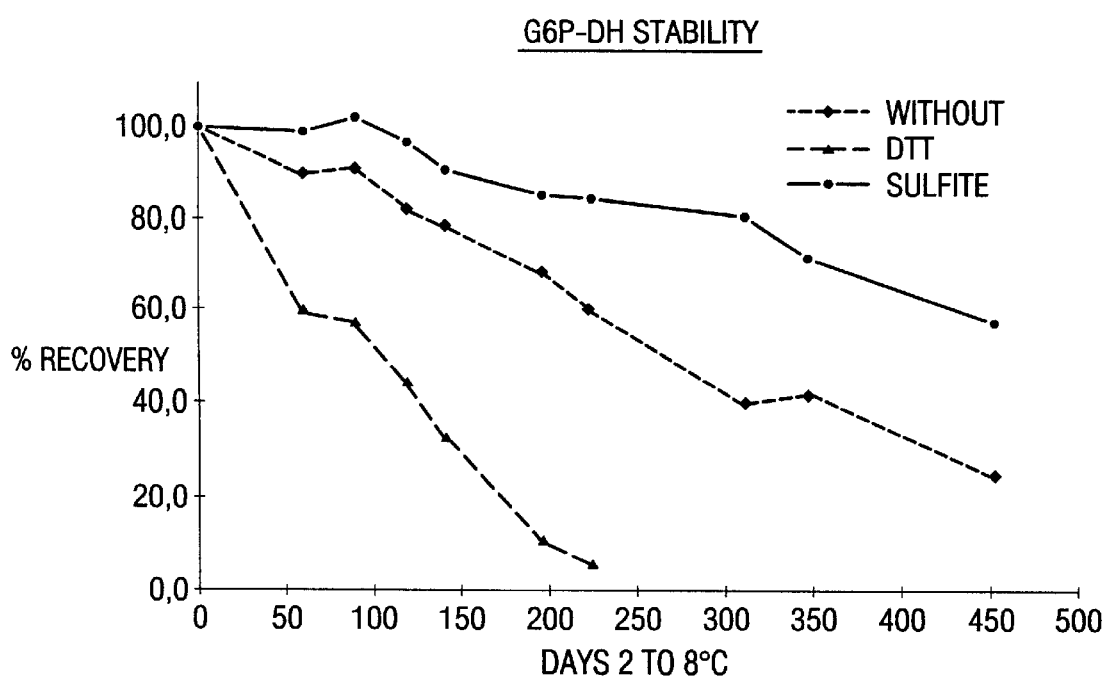

FIG. 5: Influence of $Na_2SO_3$ (1 mmol/l) compared to DTT (10 mmol/l) on G6P-DH; storage period: 136 days, temperature: 2 to 8° C.

The invention is further elucidated by the following examples:

EXAMPLE 1

Determination of CK in the Presence of $Na_2SO_3$
Reagent Composition

| | |
|---|---|
| Reagent 1 (R1): imidazole (pH 6.6) | 100 mmol/l |
| glucose | 1 mmol/l |
| magnesium acetate | 10 mmol/l |
| EDTA | 2 mmol/l |
| ADP | 2 mmol/l |
| AMP | 5 mmol/l |
| di-adenosine pentaphosphate | 10 µmol/l |
| $NADP^+$ | 2 mmol/l |
| N-acetyl cysteine | 20 mmol/l |
| hexokinase | 3 U/ml |
| G6P dehydrogenase | 3 U/ml |
| $Na_2SO_3$ | 0 to 4 mmol/l |
| Reagent 2 (R2): CAPSO (pH 9.3) | 20 mmol/l |
| glucose | 110 mmol/l |
| creatine phosphate | 170 mmol/l |

For the determination 250 µl R1 is mixed with 10 µl sample, incubated for 5 minutes, the reaction is started with 50 µl R2 and the CK activity is measured after incubating for a further 1 minute. The CK or G6P-DH enzyme activity was determined after storage at 2 to 8° C. or 35° C. for various periods (table 1–3, FIGS. 1–3).

TABLE 1

Influence of the amount of sulfite on the CK functional stability (0 to 4 mmol/l Na₂SO₃ in reagent 1) according to example 1.

| Sulfite [mmol/l] | Sample | 14 days storage at | | |
| --- | --- | --- | --- | --- |
| | | 2 to 8° C. [U/l] | 35° C. [U/l] | [%] |
| 0 | 1 | 270 | 240 | 88.9 |
| 1 | 1 | 278 | 267 | 96.0 |
| 2 | 1 | 274 | 265 | 97.0 |
| 3 | 1 | 271 | 267 | 98.5 |
| 4 | 1 | 260 | 272 | 104.4 |
| 0 | 2 | 519 | 461 | 88.9 |
| 1 | 2 | 540 | 512 | 94.8 |
| 2 | 2 | 530 | 510 | 96.2 |
| 3 | 2 | 523 | 503 | 96.2 |
| 4 | 2 | 505 | 521 | 103.1 |

TABLE 2

Influence of the amount of sulfite on the G6P-DH stability (0 to 4 mmol/l Na₂SO₃ in reagent 1) according to example 1.

| Sulfite [mmol/l] | 14 days storage at | | |
| --- | --- | --- | --- |
| | 2 to 8° C. [U/l] | 35° C. [U/l] | [%] |
| 0 | 4.01 | 1.44 | 35.9 |
| 1 | 3.95 | 1.50 | 38.1 |
| 2 | 3.92 | 1.57 | 39.9 |
| 3 | 3.98 | 1.69 | 42.5 |
| 4 | 4.06 | 1.76 | 43.5 |

TABLE 3

Long-term stability of the CK test function (0 or 1 mmol/l Na₂SO₃ in reagent 1) according to example 1

| Days 2 to 8° C. | Sample | 0 mmol/l sulfite | | 1 mmol/l sulfite | |
| --- | --- | --- | --- | --- | --- |
| | | [U/l] | [%] | [U/l] | [%] |
| 0 | 1 | 290 | 100.0 | 296 | 100.0 |
| 27 | 1 | 284 | 97.8 | 289 | 97.6 |
| 55 | 1 | 288 | 99.4 | 292 | 98.8 |
| 85 | 1 | 281 | 97.0 | 291 | 98.4 |
| 114 | 1 | 279 | 96.2 | 288 | 97.3 |
| 136 | 1 | 272 | 93.7 | 287 | 97.0 |
| 192 | 1 | 269 | 92.8 | 288 | 97.3 |
| 220 | 1 | 264 | 91.0 | 282 | 95.4 |
| 308 | 1 | 242 | 83.4 | 293 | 99.1 |
| 345 | 1 | 237 | 81.7 | 291 | 98.4 |
| 451 | 1 | 203 | 70.0 | 274 | 92.7 |
| 0 | 2 | 562 | 100.0 | 566 | 100.0 |
| 27 | 2 | 553 | 98.4 | 561 | 99.1 |
| 55 | 2 | 550 | 97.9 | 563 | 99.4 |
| 85 | 2 | 550 | 97.8 | 561 | 99.0 |
| 114 | 2 | 539 | 95.8 | 550 | 97.1 |
| 136 | 2 | 531 | 94.4 | 558 | 98.5 |
| 192 | 2 | 523 | 93.0 | 559 | 98.6 |
| 220 | 2 | 508 | 90.4 | 549 | 96.9 |
| 308 | 2 | 465 | 82.7 | 563 | 99.4 |
| 345 | 2 | 450 | 80.1 | 558 | 98.5 |
| 451 | 2 | 402 | 71.5 | 539 | 95.2 |

EXAMPLE 2

Influence of the Amount of Sulfite on the CK Activity

The reagent composition and the test procedure are essentially analogous to example 1. Only the amount of sodium sulfite (0 to 20 mmol/l) added to reagent 1 was varied. The result is shown in table 4 and FIG. 4.

TABLE 4

Influence of the amount of sulfite on the CK function (0 to 20 mmol/l Na₂SO₃ in reagent 1)

| Sulfite [mmol/l test] | Sample 1 | | Sample 2 | |
| --- | --- | --- | --- | --- |
| | [U/l] | [%] | [U/l] | [%] |
| 0 | 236 | 100.0 | 529 | 100.0 |
| 1 | 242 | 102.9 | 530 | 100.2 |
| 2 | 239 | 101.4 | 520 | 98.4 |
| 3 | 236 | 100.3 | 514 | 97.2 |
| 4 | 227 | 96.4 | 496 | 93.8 |
| 5 | 215 | 91.3 | 504 | 95.3 |
| 10 | 196 | 83.2 | 464 | 87.7 |
| 20 | 182 | 77.3 | 441 | 83.3 |

EXAMPLE 3

Reagent Stability in the Presence of Dithiothreitol (DTT) (Prior Art)

Reagent Composition

| | |
| --- | --- |
| Reagent (R): imidazole (pH 6.6) | 100 mmol/l |
| glucose | 1 mmol/l |
| magnesium acetate | 10 mmol/l |
| EDTA | 2 mmol/l |
| adenosine 5'-diphosphate | 2 mmol/l |
| adenosine 5'-monophosphate | 5 mmol/l |
| di-adenosine pentaphosphate | 10 μmol/l |
| NADP⁺ | 2 mmol/l |
| N-acetyl cysteine | 20 mmol/l |
| hexokinase | 3 U/ml |
| G6P dehydrogenase | 3 U/ml |
| dithiothreitol | 10 mmol/l |

The reagent R was combined with the sample to be measured as described in example 1 and the corresponding enzyme activities were determined (table 5, FIG. 5).

TABLE 5

Long-term stability G6P-DH (10 mmol/l DTT compared to 1 mmol/l Na₂SO₃, example 1)

| Days 2 to 8° C. | without example 1 | | 1 mmol/l sulfite example 1 | | 10 mmol/l DTT example 3 | |
| --- | --- | --- | --- | --- | --- | --- |
| | U/ml | % | U/ml | % | U/ml | % |
| 0 | 3.84 | 100.0 | 3.68 | 100.0 | 4.67 | 100.0 |
| 55 | 3.46 | 90.3 | 3.65 | 99.2 | 2.81 | 60.2 |
| 85 | 3.51 | 91.4 | 3.77 | 102.3 | 2.69 | 57.6 |
| 114 | 3.16 | 82.4 | 3.57 | 96.9 | 2.07 | 44.4 |
| 136 | 3.03 | 78.9 | 3.35 | 91.0 | 1.55 | 33.1 |
| 192 | 2.64 | 68.8 | 3.15 | 85.5 | 0.52 | 11.1 |
| 220 | 2.34 | 60.4 | 3.12 | 84.7 | 0.29 | 6.2 |
| 308 | 1.55 | 40.4 | 2.98 | 80.9 | — | — |
| 345 | 1.60 | 41.7 | 2.65 | 72.0 | — | — |
| 451 | 0.96 | 25.0 | 2.12 | 57.6 | — | — |

EXAMPLE 4

Regeneration of CK in Reagent 1

Reagent Composition

| | |
|---|---|
| Reagent 1 (R1): imidazole (pH 6.6) | 100 mmol/l |
| glucose | 1 mmol/l |
| magnesium acetate | 10 mmol/l |
| EDTA | 2 mmol/l |
| ADP | 2 mmol/l |
| AMP | 5 mmol/l |
| di-adenosine pentaphosphate | 10 μmol/l |
| NADP$^+$ | 2 mmol/l |
| N-acetyl cysteine | 20 mmol/l |
| hexokinase | 3 U/ml |
| G6P dehydrogenase | 3 U/ml |
| Reagent 2 (R2): CAPSO (pH 9.3) | 20 mmol/l |
| glucose | 110 mmol/l |
| creatine phosphate | 170 mmol/l |
| Na$_2$SO$_3$ | 10 mmol/l |

The mixing of R1, R2 and the respective sample and the subsequent determination were carried out according to example 1.

TABLE 6

Regeneration of the CK in R1 by adding sulfite in R2

| R1 | R2 | | | recovery | |
|---|---|---|---|---|---|
| stress 14 days | sulfite [mmol/l] | sample 1 [U/l] | sample 2 [U/l] | sample 1 [%] | sample 2 [%] |
| reagent fresh (reference) | | 236 | 513 | | |
| 2–8° C. | 0 | 228 | 494 | 96.6 | 96.2 |
| | 10 | 238 | 509 | 100.8 | 99.5 |
| 35° C. | 0 | 179 | 382 | 75.8 | 74.4 |
| | 10 | 227 | 486 | 96.2 | 94.7 |

We claim:

1. A reagent for the determination of creatine kinase in a biological sample comprising a first partial reagent comprising substrates and coenzymes that can be converted by said creatine kinase and a creatine kinase activator in an aqueous buffered medium, and a second partial reagent comprising a sulphur component selected from the group consisting of reducing inorganic sulphur compounds and sulphur salts, said sulphur component being present in a submolar amount relative to said creatine kinase activator and absent from said first partial reagent and said first or second partial reagent further comprising creatine phosphate.

2. The reagent of claim 1, wherein said sulphur component carries a negative charge.

3. The reagent of claim 1, wherein said sulphur component is present in an amount less than 20 mmol/l.

4. The reagent of claim 1, wherein said sulphur component is selected from the group consisting of dithionite, pyrosulphuric acid, polythionic acid and salts thereof and thiosulfate and sulfite salts of alkali or alkaline earth ions.

5. The reagent of claim 1, wherein said first or second partial reagent further comprises a compound selected from the group consisting of creatine phosphate, glucose, glucose-6-phosphate dehydrogenase, adenosine-5'-diphosphate, a glucose-6-phosphate-forming enzyme, NAD$^+$ or NADP$^+$, and an adenylate kinase inhibitor.

6. A reagent for the determination of creatine kinase in a biological sample comprising a first partial reagent comprising glucose, glucose-6-phosphate dehydrogenase, adenosine-5'-diphosphate, a hexokinase, NAD$^+$ or NADP$^+$ and a creatine kinase activator in an aqueous buffered medium, and a second partial reagent comprising creatine phosphate and a sulphur component selected from the group consisting of reducing inorganic sulphur compounds and sulphur salts, said sulphur component being present in a submolar amount relative to said creatine kinase activator and absent from said first partial reagent.

7. The reagent of claim 6, wherein said glucose is present at a maximum concentration of 5 mmol/l.

8. A method for the enzymatic determination of creatine kinase in a biological sample, said method comprising:

a. forming a reaction mixture by combining said sample with a first partial reagent comprising substrates and coenzymes that can be converted by said creatine kinase to form a measurable product, b. adding to said reaction mixture a second partial reagent comprising a sulphur component selected from the group consisting of reducing inorganic sulphur compounds and sulphur salts, said sulphur component being present in a submolar amount relative to said creatine kinase activator and absent from said first partial reagent, and said first or second partial reagent further comprising creatine phosphate, and c. detecting the product formed as a measure of said creatine kinase present in said sample.

9. The method of claim 8, wherein said sulphur component carries a negative charge.

10. The method of claim 8, wherein said sulphur component is present in an amount less than 20 mmol/l.

11. The method of claim 8, wherein said sulphur component is selected from the group consisting of dithionite, pyrosulphuric acid, polythionic acid and salts thereof and thiosulfate and sulfite salts of alkali or alkaline earth ions.

12. The method of claim 8, wherein said first or second partial reagent further comprises a compound selected from the group consisting of creatine phosphate, glucose, glucose-6-phosphate dehydrogenase, adenosine-5'-diphosphate, a glucose-6-phosphate-forming enzyme, NAD$^+$ or NADP$^+$, and an adenylate kinase inhibitor.

13. A method for the enzymatic determnination of creatine kinase in a biological sample, said method comprising:

a. forming a reaction mixture by combining said sample with a first artial reagent comprising glucose, glucose-6-phosphate dehydrogenase, adenosine-5'-diphosphate, a hexokinase, NAD$^+$ or NADP$^+$ and a creatine kinase activator in an aqueous buffered medium, b. adding to said reaction mixture a second partial reagent comprising creatine phosphate and a sulphur component selected from the group consisting of reducing inorganic sulphur compounds and sulphur salts, said sulphur component being present in a submolar amount relative to said creatine kinase activator and absent from said first partial reagent, and c. detecting the NADH or NADPH formed as a measure of said creatine kinase present in isaid sample.

14. The method of claim 13, wherein said glucose is present at a maximum concentration of 5 mol/l.

* * * * *